(12) United States Patent
Watanabe

(10) Patent No.: US 10,321,828 B2
(45) Date of Patent: *Jun. 18, 2019

(54) OBJECT INFORMATION ACQUIRING APPARATUS AND CONTROL METHOD FOR THE OBJECT INFORMATION ACQUIRING APPARATUS

(71) Applicant: CANON KABUSHIKI KAISHA, Tokyo (JP)

(72) Inventor: Tadaki Watanabe, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 124 days.

This patent is subject to a terminal disclaimer.

(21) Appl. No.: 15/298,635

(22) Filed: Oct. 20, 2016

(65) Prior Publication Data

US 2017/0035300 A1 Feb. 9, 2017

Related U.S. Application Data

(63) Continuation of application No. 14/068,090, filed on Oct. 31, 2013, now Pat. No. 9,513,262.

(30) Foreign Application Priority Data

Nov. 12, 2012 (JP) ................. 2012-248341

(51) Int. Cl.
*G01N 29/26* (2006.01)
*G01N 29/06* (2006.01)
(Continued)

(52) U.S. Cl.
CPC .......... *A61B 5/0095* (2013.01); *A61B 5/4312* (2013.01); *G01N 29/0654* (2013.01);
(Continued)

(58) Field of Classification Search
CPC .. G01N 29/26; G01N 29/0654; G01N 29/262; G01N 29/2418; G01N 29/032;
(Continued)

(56) References Cited

U.S. PATENT DOCUMENTS

| 4,690,150 A | 9/1987 | Mayo, Jr. ........................ 128/660 |
| 5,241,473 A | 8/1993 | Isihara et al. ............ 364/413.25 |

(Continued)

FOREIGN PATENT DOCUMENTS

| JP | A 2003-230560 | 8/2003 |
| JP | A 2010-02812 | 2/2010 |

(Continued)

*Primary Examiner* — Helen C Kwok
(74) *Attorney, Agent, or Firm* — Venable LLP

(57) ABSTRACT

An object information acquiring apparatus comprises a receiver receiving an acoustic wave propagating inside an object and convert the acoustic wave into an electric signal; a scanning unit configured to causing the receiver to scan the object; a control unit configured to controlling operation of the scanning unit; a detection unit configured to detecting a status of the acoustic wave reception; and a processing unit for acquiring characteristic information on the inside of the object on the basis of the electric signal, wherein the control unit decides whether or not the operation of the scanning unit is changed, on the basis of a result of detection by the detection unit.

27 Claims, 4 Drawing Sheets

(51) Int. Cl.
*A61B 5/00* (2006.01)
*G01N 29/22* (2006.01)
*G01N 29/24* (2006.01)

(52) U.S. Cl.
CPC ....... *G01N 29/223* (2013.01); *G01N 29/2418* (2013.01); *G01N 29/26* (2013.01); *G01N 29/262* (2013.01); *A61B 2560/0276* (2013.01); *G01N 2291/02475* (2013.01); *G01N 2291/26* (2013.01)

(58) Field of Classification Search
CPC .. G01N 29/024; A61B 5/0095; A61B 5/0091; A61B 5/6843; A61B 5/708; A61B 5/4312; A61B 5/748; A61B 5/7228; A61B 8/14; A61B 8/5238; A61B 8/08; A61B 8/0841; A61B 8/4427; A61B 8/4483; A61B 8/467
See application file for complete search history.

(56) References Cited

U.S. PATENT DOCUMENTS

| | | | |
|---|---|---|---|
| 5,479,259 A | 12/1995 | Nakata et al. | 356/349 |
| 6,095,978 A | 8/2000 | Takeucki | 29/25.35 |
| 6,677,985 B1 | 1/2004 | Kubota et al. | 348/77 |
| 6,709,393 B2 | 3/2004 | Ogawa | 356/479 |
| 7,421,900 B2 | 9/2008 | Karasawa et al. | 73/621 |
| 8,429,973 B2 | 4/2013 | Isobe et al. | 73/602 |
| 8,485,977 B2 | 7/2013 | Hirama | 600/447 |
| 9,513,262 B2 * | 12/2016 | Watanabe | G01N 29/0654 |
| 2002/0138005 A1 | 9/2002 | Ogawa | 600/443 |
| 2010/0058870 A1 | 3/2010 | Kobayashi | 73/596 |
| 2010/0286519 A1 | 11/2010 | Lee et al. | 600/439 |
| 2011/0066023 A1 | 3/2011 | Kanayama | 600/407 |
| 2011/0098550 A1 | 4/2011 | Yoda | 600/407 |
| 2011/0172532 A1 | 7/2011 | Yoo et al. | 600/443 |
| 2011/0190617 A1 | 8/2011 | Chen | 600/439 |
| 2012/0203093 A1 | 8/2012 | Imran et al. | 600/407 |
| 2012/0220844 A1 | 8/2012 | Baker, Jr. | 600/328 |
| 2013/0010137 A1 | 1/2013 | Kawai | 348/208.1 |
| 2013/0044563 A1 | 2/2013 | Watanabe et al. | 367/7 |
| 2013/0123604 A1 | 5/2013 | Oyama | 600/407 |
| 2013/0123627 A1 | 5/2013 | Oyama | 600/442 |
| 2013/0261427 A1 | 10/2013 | Oioshi | 600/407 |
| 2013/0267856 A1 | 10/2013 | Watanabe et al. | 600/476 |
| 2014/0130600 A1 | 5/2014 | Watanabe | 73/619 |
| 2014/0303498 A1 | 10/2014 | Watanabe et al. | 600/437 |
| 2015/0000411 A1 | 1/2015 | Watanabe et al. | 73/643 |

FOREIGN PATENT DOCUMENTS

| | | |
|---|---|---|
| JP | A 2010-022812 | 2/2010 |
| JP | A 2010-094171 | 4/2010 |

* cited by examiner

OBJECT INFORMATION ACQUIRING APPARATUS AND CONTROL METHOD FOR THE OBJECT INFORMATION ACQUIRING APPARATUS

RELATED APPLICATIONS

This application is a continuation of application Ser. No. 14/068,090, filed Oct. 31, 2013. It claims benefit of that application under 35 U.S.C. § 120, and claims benefit under 35 U.S.C. § 119 of Japanese Patent Application No. 2012-248341, filed on Nov. 12, 2012. The entire contents of each of the mentioned prior applications are incorporated herein by reference.

BACKGROUND OF THE INVENTION

Field of the Invention

The present invention relates to an object information acquiring apparatus and a control method thereof.

Description of the Related Art

There is photo acoustic imaging (PAI) as one of optical imaging techniques using light. In the photo acoustic imaging, pulsed light is applied to an object such as a biological body, and an acoustic wave generated by a segment to be tested (e.g., a light absorber such as a tumor) which absorbs optical energy is received by a receiver. Then, an analytical process is performed for a reception signal output from the receiver, thereby obtaining an optical property distribution of the inside of the object as image data.

Japanese Patent Application Laid-open No. 2010-022812 discloses an apparatus for receiving an acoustic wave while holding a breast from both sides with holding members and performing two-dimensional scanning on the holding member with the receiver.

The receiver two-dimensionally scans, so that pieces of characteristic information at a plurality of positions inside an object can be obtained.

Like the apparatus described in Japanese Patent Application Laid-open No. 2010-022812, in a case of an apparatus in which the receiver performs two-dimensional scanning in a main scanning direction and a sub-scanning direction, and acquires acoustic waves in a desired region, an error may occur before scanning and acoustic wave acquisition for the overall desired region are completed. Possible error includes an error resulting from an apparatus, a human error, and the like. Hereinafter, scanning with the receiver for acquiring an acoustic wave will be described as photographing.

In a case where an error occurs, photographing may be able to restart immediately depending on the contents of the error. Even though the photographing can restart immediately, and the condition of the photographing remains almost unchanged, in a case where the receiver is returned to a position where the photographing started, and photographing starts again without determination of the contents of the error, it takes time to acquire acoustic waves in the desired region.

Particularly, in a case where the region for acquiring acoustic waves are large, when scanning is performed from an initial position with the receiver again, a photographing time is greatly increased, and a binding time for a subject is increased. However, heretofore, there is no means for controlling the receiver on the basis of information such as the content of an error for re-photographing.

SUMMARY OF THE INVENTION

The present invention has been conceived in order to solve the aforementioned problem, and an object thereof is to suppress increase in a photographing time by re-photographing in accordance with the content of an error, even in a case where the error occurs when characteristic information of the inside of an object is being acquired by scanning with a receiver.

The present invention in its one aspect provides an object information acquiring apparatus comprising a receiver receiving an acoustic wave propagating inside an object and convert the acoustic wave into an electric signal; a scanning unit configured to causing the receiver to scan the object; a control unit configured to controlling operation of the scanning unit; a detection unit configured to detecting a status of the acoustic wave reception; and a processing unit for acquiring characteristic information on the inside of the object on the basis of the electric signal, wherein the control unit decides whether or not the operation of the scanning unit is changed, on the basis of a result of detection by the detection unit.

The present invention in its another aspect provides a control method for an object information acquiring apparatus, the method comprising operating a receiver to receive an acoustic wave propagating inside an object and convert the acoustic wave into an electric signal, with a receiver; operating a scanning unit to cause the receiver to scan the object; operating a control unit to control operation of the scanning unit; operating a detection unit to detect a status of the reception of the acoustic wave; and an operating processing unit to acquire characteristic information on inside of the object on the basis of the electric signal, wherein in the step of controlling, decision is made on whether or not the operation of the scanning unit is changed, on the basis of a result of detection by the detection unit.

According to the present invention, it is possible to suppress increase in a photographing time by re-photographing in accordance with a content of an error, even in a case where the error occurs when characteristic information of the inside of an object is being acquired by scanning with a receiver.

Further features of the present invention will become apparent from the following description of exemplary embodiments with reference to the attached drawings.

DESCRIPTION OF THE EMBODIMENTS

Figure 1:
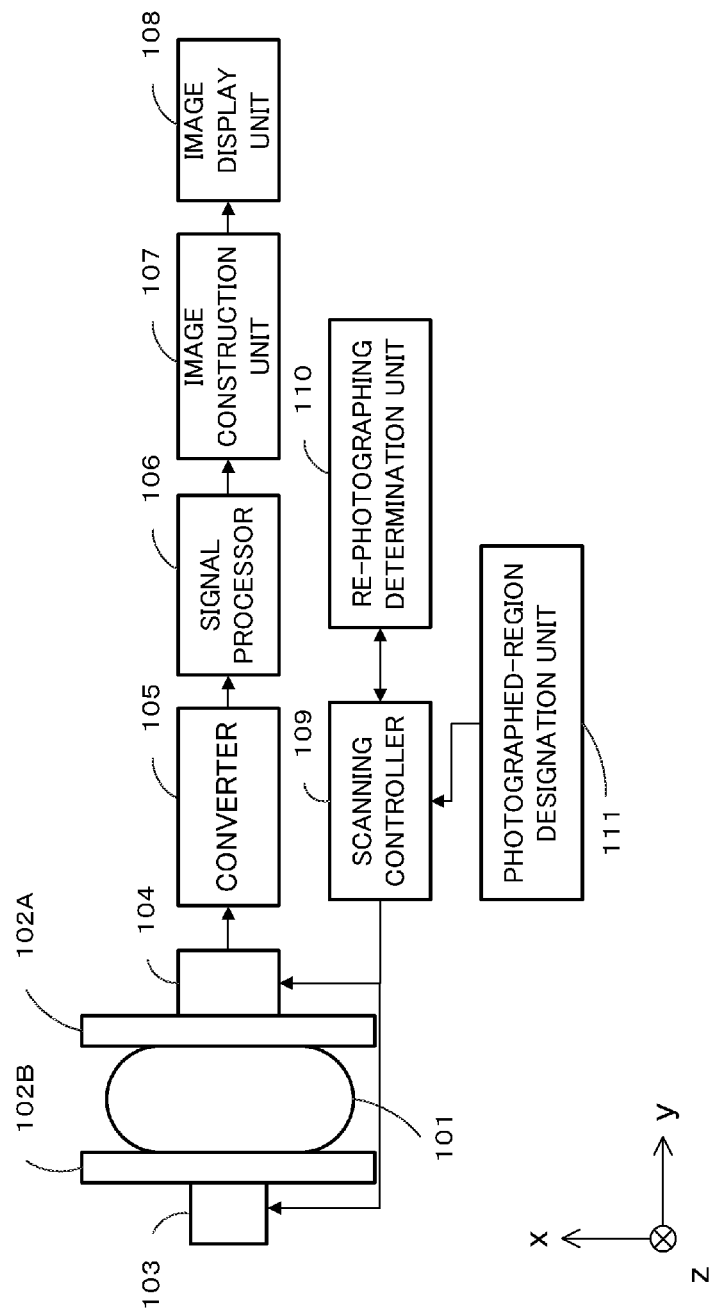
FIG. 1 is a block diagram of an object information acquiring apparatus to which the present invention can be applied.

Hereinafter, preferred embodiments of the present invention will be described with reference to the drawings. However, size, quality of materials, and shape of components described below, relative arrangement of these, and the like should be appropriately changed according to a configuration of an apparatus to which the invention is applied, or various conditions, and the scope of this invention is not limited to the description described below.

In the present invention, an acoustic wave includes an elastic wave referred to as a sound wave, an ultrasound wave, a photoacoustic wave, or a light-induced ultrasound wave, and a receiver receives an acoustic wave propagated inside an object. That is, an object information acquiring apparatus of the present invention includes an apparatus which utilizes a photoacoustic effect of receiving an acoustic wave generated inside an object by applying light (electromagnetic wave) to the object to acquire characteristic information of the inside of the object.

In a case of the apparatus utilizing an photoacoustic effect, the acquired characteristic information of the inside of an object indicates object information reflecting initial sound pressure of an acoustic wave generated by light application, or optical energy absorption density derived from the initial sound pressure, an absorption coefficient, concentration of substances configuring tissues, etc. The concentration of the substances includes an oxygen saturation degree or oxyhemoglobin/deoxyhemoglobin concentration, and the like, for example. The characteristic information may be acquired not as numerical data but as distribution information of each of positions inside the object. That is, distribution information such as an absorption coefficient distribution or an oxygen saturation distribution may be acquired as image data.

The object information acquiring apparatus of the present invention may be an apparatus which utilizes an ultrasound wave echo technique of transmitting an ultrasound wave to an object, receiving a reflected wave that is reflected on the inside of the object, and acquiring characteristic information of the inside of the object. In a case of the apparatus which utilizes this ultrasound wave echo technique, the acquired characteristic information is information reflecting difference in acoustic impedance of tissues inside the object.

The present invention can be grasped as a control method used when the object information acquiring apparatus receives an acoustic wave.

The details will be described in respective embodiments. The present invention is characterized in that in a case where an error occurs when an acoustic wave is being acquired, it is determined whether or not re-photographing is possible in accordance with a content of the error. In a case where the re-photographing is possible, a re-photographing method is decided on the basis of a position of a receiver at the occurrence of the error, the content of the error, and photographed size. Note that the same components are generally denoted by the same reference numerals, and description thereof will be omitted.

<First Embodiment>

An apparatus of this embodiment causes a receiver for receiving an acoustic wave generated by a photoacoustic effect to perform scanning in a main scanning direction and a sub-scanning direction. The sub-scanning direction intersects with the main scanning direction, and is typically orthogonal to the main scanning direction. In a case where an error occurs when an acoustic wave is being acquired, the apparatus determines whether or not re-photographing is possible, in accordance with a content of the error. In a case where the re-photographing is possible, re-photographing is performed on the basis of a position of the receiver at the occurrence of the error, the content of the error, and photographed size. Hereinafter, a basic configuration and a function of the apparatus will be first described, and thereafter, a method of re-photographing in an error which is a characteristic of the present invention will be described.

(Basic Configuration of Apparatus)

FIG. 1 is a schematic diagram showing a configuration of an object information acquiring apparatus according to a first embodiment.

The object information acquiring apparatus of the this embodiment includes holding members 102 for holding a biological body 101 being an object, an irradiation unit 103 for applying light, a receiver 104 for receiving an acoustic wave to convert the same into a reception signal, and a converter 105 for amplifying the reception signal to convert the amplified reception signal into a digital signal. Furthermore, the object information acquiring apparatus includes a signal processor 106 for performing an integration process of the digitalized reception signal or the like, an image construction unit 107 for generating image data by using an output signal from the signal processor, and an image display unit 108 for displaying an image generated by the image construction unit 107. Moreover, the object information acquiring apparatus includes a scanning controller 109 for the irradiation unit 103 and the receiver 104, and a re-photographing determination unit 110 for determining a reason in a case where photographing fails due to an error, and transmitting information necessary for re-photographing to the scanning controller 109.

(Holding Member)

As the biological body 101, for example, a breast may be used. The holding members 102 are configured by a pair of two of a first holding member 102A and a second holding member 102B, and holds the biological body 101 from both sides. A relative position between the both holding members is controlled by a holding mechanism (not shown) for changing a holding gap and holding pressure. In the following description, in a case where the holding members 102A and 102B do not need to be distinguished, the holding members 102A and 102B are collectively represented by the holding members 102. The object is not limited to a biological body, and various objects including a pseudo biological body such as a phantom can be measured.

The biological body 101 is sandwiched between the holding members 102 to be fixed, so that a measurement error resulting from movement of the biological body 101 can be reduced. Additionally, the biological body 101 can be adjusted to a desired thickness according to the degree of penetration depth of light. Since the holding member 102B is located on an optical path from the irradiation unit 103, a material having high transmittance with respect to used light, such as polymethylpentene is preferable as the material of the holding member 102B. Additionally, the holding member 102A on the receiver 104 side is preferably a member having high acoustic consistency with the receiver 104. After adjusting the position or the shape of the biological body 101 with manipulation, a user fixes the holding members 102.

(Irradiation Unit)

The irradiation unit 103 for applying light to the biological body 101 is configured from a light source for generating light, and an irradiation unit for applying the light to an object from the light source. As the light source, a solid-state laser capable of generating pulsed light (pulse width of 100 nsec or less) having a center wavelength on a near-infrared region of 530 to 1300 nm is preferable. For example, Yttrium-Aluminium-Garnet laser or Titan-Sapphire laser is used. The wavelength of measurement light is selected between 530 nm and 1300 nm in accordance with light absorbing substances (e.g., hemoglobin, glucose, cholesterol, etc.) inside a biological body being an object to be measured.

Examples of the irradiation unit include, for example, a mirror for reflecting light, a lens for changing the shape of light by collecting and/or enlarging the light, a prism for dispersing, refracting, and/or reflecting light, and an optical fiber for propagating light, and a diffuser panel. As long as light generated from the light source is applied to a desired region in an object so as to have a desired shape, any irradiation unit may be employed. A position of an emission end of light (i.e., irradiated region) from the irradiation unit is controlled by the scanning controller 109.

(Receiver)

The receiver 104 includes an element for receiving an acoustic wave to convert the same into an electric signal (reception signal). Examples of the element of the receiver 104 include a conversion element using a piezoelectric phenomenon, a conversion element using resonance of light, a conversion element using change in electrostatic capacitance, and the like. Any element capable of receiving an acoustic wave to convert the same into an electric signal may be used. The receiver 104 includes a plurality of elements in a one-dimensional manner or two-dimensional manner, so that reduction in a measurement time or improvement of measurement accuracy can be expected.

Since the sound pressure of the generated acoustic wave is proportional to the light intensity of light, light is preferably applied to a region on a front surface of the receiver in order to improve the signal-to-noise ratio (SNR) of a reception signal. Therefore, the emission end of light of the irradiation unit 103 and the receiver 104 are preferably arranged at such opposed positions as to sandwich an object therebetween. In order to achieve such arrangement, the scanning controller 109 causes the emission end of light and the receiver 104 to scan in synchronization while maintaining the positional relation between the receiver 104 and the emission end of light. The irradiation unit guides light also to the receiver 104 side, so that light may be applied to the biological body 101 also from the same side as the receiver 104.

(Converter)

The converter 105 is configured from a signal amplifier for amplifying an analog signal (analog reception signal) input from the receiver 104, and an A/D converter for converting an analog signal into a digital signal. The signal amplifier controls increase/reduction in amplification gain, etc. in accordance with time from when light is applied until when an acoustic wave reaches the elements of the receiver, so as to obtain image data with uniform contrast regardless of the depth degree in the inside of the biological body. An analog reception signal converted from a photoacoustic wave, or a digital signal for which A/D conversion is performed is also referred to as a photoacoustic signal.

(Signal Processor)

The signal processor 106 performs sensitivity variation correction of elements for a digital reception signal output from the converter 105, a complementary process of an element which is physically or electrically lost, a recording operation to a recording medium (not shown), an integration process for noise reduction, and the like. In the integration process which is performed in order to improve the SNR of the reception signals, an acoustic wave is repeatedly received at the same position with respect to the biological body 101, and reception signals are averaged, thereby reducing system noise. A processing means in the present invention corresponds to the signal processor.

(Image Construction Unit)

The image construction unit 107 is a characteristic information acquisition unit for acquiring a distribution (property distribution such as an absorption coefficient distribution and an oxygen saturation distribution) indicating optical characteristic information at each position inside the biological body 101, as image data, by using a signal output from the signal processor 106. Additionally, the image construction unit 107 may generate image data more preferable for diagnosis, by applying various correction processes such as adjustment of brightness, distortion correction, and cut-out of an attention region, to the generated image data.

(Image Display Unit)

The image display unit 108 displays an image of a property distribution on the basis of image data input from the image construction unit 107.

(Scanning Controller)

As described above, the scanning controller 109 controls scanning positions of the emission end of light and the receiver 104. Therefore, a mechanism for operating in accordance with control exists. These two-dimensionally scan the biological body 101 to receive an acoustic wave at each scanning position, so that even a compact receiver can obtain a wide range of characteristic information. A range in which the emission end of light and the receiver 104 perform scanning is decided in accordance with a result of control by a photographed-region designation unit 111 which will be described later. The scanning controller 109 holds a current scanning position of the receiver 104, a position of the receiver 104 at a photographing start point, a position where the receiver 104 starts scanning at each stripe, and a scanning range of the receiver 104 at photographing. A mechanism where the scanning controller causes the receiver and the emission end to move corresponds to scanning means in the present invention.

When an error occurs, the scanning position is changed in accordance with a result of control by the re-photographing determination unit 110 which will be described later. The stripe is a region where acoustic waves can be received by a single scanning or a predetermined number of times of scanning in the main scanning direction. In a case where an object is wider compared to the receiver size, measurement can be performed over the overall region by dividing the object into a plurality of stripes.

(Photographed-region Designation Unit)

The photographed-region designation unit 111 is input means for designating a photoacoustic acquisition region (acoustic wave acquisition region) by a user. The photoacoustic acquisition region indicates an acquisition range of three-dimensional photoacoustic signal in the object that is held by the holding members 102. As the photographed-region designation unit 111, a pointing device such as a mouse and a key board, a pen tablet or the like can be utilized. The photoacoustic acquisition region that is input by the user herein is transmitted to the scanning controller 109, as described above. Then, the scanning controller 109 controls the scanning positions of the emission end of light and the receiver 104 such that a signal in the photoacoustic acquisition region can be acquired. The photographed-region designation unit corresponds to designation means in the present invention.

(Re-photographing Determination Unit)

The re-photographing determination unit 110 monitors the overall object information acquiring apparatus. The details thereof will be later described. In a case where an error occurs during photographing by the object information acquiring apparatus, the re-photographing determination unit 110 determines whether or not re-photographing is possible, in accordance with a content of the error. Then, in a case where the re-photographing is possible, the re-photographing determination unit 110 decides a position where the receiver 104 restarts photographing, on the basis of a position of the receiver at occurrence of the error, the content of the error, the size of the photoacoustic acquisition region that is input by a user using the photographed-region designation unit 111, and transmits the decision to the scanning controller 109. Additionally, the re-photographing determination unit 110 acquires detailed information on the occurrence of the error from each unit configuring the object information acquiring apparatus, at the time of the occurrence of the error. The re-photographing determination unit corresponds to control means in the present invention. Additionally, it can be conceived that the control means includes a control process performed by the scanning controller.

(Scanning Control of Receiver)

Figure 2:
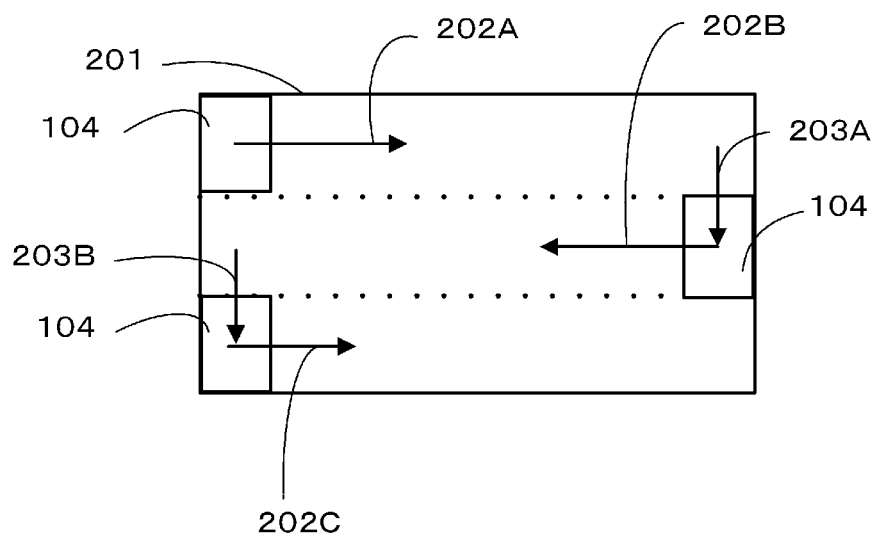
FIG. 2 is a conceptual diagram showing movement of a receiver of the present invention.

FIG. 2 shows a state where the receiver 104 performs scanning in a photoacoustic acquisition region 201. In FIG. 2, a scanning range by the receiver 104 on the holding member 102A, based on a photoacoustic signal acquisition region being a three-dimensional range is denoted by a reference numeral 201.

The receiver 104 performs scanning in a main scanning direction 202 and a sub-scanning direction 203 so as to receive a photoacoustic signal in the photoacoustic acquisition region 201. First, the receiver 104 moves in a main scanning direction 202A from an initial position located upper left in the photoacoustic acquisition region 201, to acquire a photoacoustic signal of an uppermost stripe. When reaching upper right, the receiver 104 moves in a sub-scanning direction 203A by a predetermined sub-scanning distance.

Next, the receiver 104 moves in a main scanning direction 202B to acquire a photoacoustic signal of a middle stage stripe. When reaching a left end of the middle stage, the receiver 104 moves in the sub-scanning direction 203B to reach a lowermost stage, and moves in a main scanning direction 202C. The predetermined sub-scanning distance is equal to the width of the receiver 104 herein, but is not limited to this. For example, an overlapped portion between the stripes in the sub-scanning direction may exist. The receiver 104 scans the same stripe a plurality of times, and thereafter moves to a next stripe, so that the SNR can be improved.

(Flow of Re-photographing Method in Error)

Figure 3:
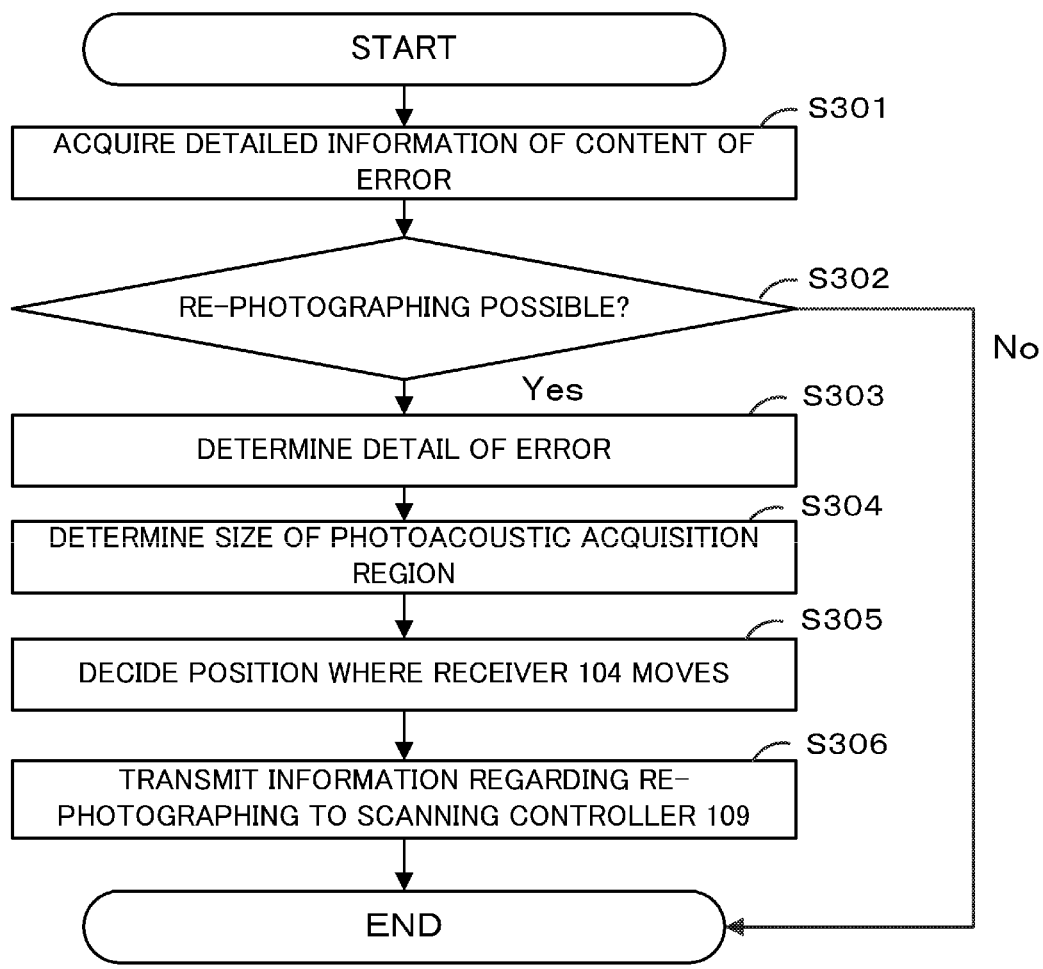
FIG. 3 is a flowchart showing an example of a re-photographing method of the present invention.

A flow of processes of re-photographing control performed in a case where an error occurs during scanning shown in FIG. 2 will be described with reference to FIG. 3. FIG. 3 is a flowchart of re-photographing according to this embodiment, and the re-photographing starts from a situation where an error occurs.

An error in this flow occurs because it is detected that the light quantity is at a level not suitable for measurement. Such a phenomenon occurs, for example, when the oscillation of light from the light source of the irradiation unit 103 becomes unstable. The light quantity whose level is not suitable for measurement is, for example, such a small light quantity that an acoustic wave with intensity necessary for accurate characteristic information does not generate, and a predetermined standard is not satisfied.

In Step S301, the re-photographing determination unit 110 detects that an error occurs during photographing. Then, the re-photographing determination unit 110 collects information from each unit in the object information acquiring apparatus to acquire the detail of the error. The re-photographing determination unit 110 acquires, from the scanning controller 109, information that the light quantity whose level is not suitable for measurement is detected. This error detection can be achieved, for example, by arranging an optical sensor on the scanning controller 109, monitoring the light quantity, and transmitting a result of detection. In this case, it can be conceived that combination of the optical sensor, and the re-photographing determination unit for determining an error on the basis of sensor information is detection means in the present invention. Similarly, it can be said that each of various sensors according to the types of errors, and the re-photographing determination unit are the detection means in the present invention.

In Step S302, the re-photographing determination unit 110 determines whether or not the error is such an error that re-photographing is possible, on the basis of the detail of the error acquired in Step S301.

Examples of the error where re-photographing is possible are as follows. First, as shown in this flow, an error occurs in a case where the oscillation of light from the light source of the irradiation unit 103 becomes unstable, and it is detected that the level of the light quantity is not suitable for measurement.

Another example is abnormality of communication in each unit configuring the object information acquiring apparatus. This error is detectable by a circuit for detecting a status of communication of each unit, etc.

Additionally, an error occurs in a case where a door (not shown) installed in a housing of an apparatus is opened in order to perform the aforementioned manipulation of the biological body 101. This error is detectable by a contact sensor (physical or optical sensor).

Furthermore, an error occurs in a case where an accuracy error exists between a position of the emission end of light of the irradiation unit 103, and a scanning position of the receiver 104, the receiver 104 and the emission end of light being caused to perform scanning in synchronization by the scanning controller 109. This error is detectable by, for example, a meter for detecting a position.

Results of detection by these sensors each may include not only the fact that an error occurs but also a difference from a predetermined value or continuity of a phenomenon detected as an error.

If the error is an error where photographing can immediately start, it is determined that re-photographing is possible (S302=Yes). The error in this flow is determined as an error where re-photographing is possible. On the other hand, if re-photographing is impossible, the flow is terminated (S302=No).

If it is determined that re-photographing is possible, it is decided where the receiver 104 moves, on the basis of the detail of the error, the a current position of the receiver 104, and the size of a photoacoustic acquisition region designated by a user with the photographed-region designation unit 111, in Step S303 to S305.

Figure 4:
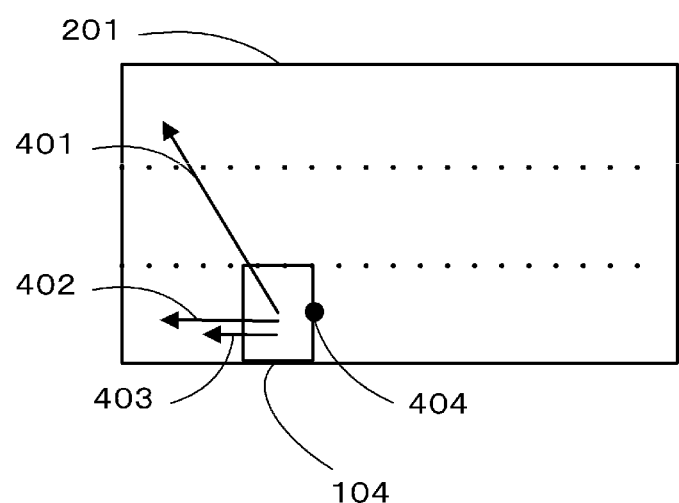
FIG. 4 is a conceptual diagram showing a start position of the re-photographing of the present invention.

Examples of a candidate of a position where the receiver 104 moves includes, as shown in FIG. 4, a position 401 of the receiver 104 at a photographing start point, a start point 402 of a stripe for which photographing is currently being performed, and a position 403 just before an error occurs. In the figure, it is assumed that the error occurs at an error occurrence point 404.

In Step S303, the re-photographing determination unit 110 determines the detail of the error. That is, it is determined whether or not the error that has occurred is an error that continuously influences acquisition of a photoacoustic signal during scanning of a stripe, among various errors where re-photographing is possible. In a case where the error that has occurred is applicable to this, the necessity arises for the receiver 104 to implement re-photographing by moving to the start point 402 of a stripe, for which photographing is currently undergoing. An example of this error includes, for example, a case where the oscillation of light form the light source continuously becomes unstable during scanning by receiver 104. As another example, there is a case where an accuracy error between scanning positions of the emission end of light and the receiver 104 in the scanning controller 109 is continuously increased.

In a case of such a continuous error, in Step S305 which will be described later, a destination of the receiver 104 is decided as the start point 402 of a stripe for which photographing is being performed. This positional information is the same as a position of the receiver 104 held by the scanning controller 109, at a photographing start point of a stripe. The re-photographing determination unit 110 transmits, to the scanning controller 109, indication information that scanning restarts from the position 402.

The error where the oscillation of the light from the light source becomes unstable and the level that is not suitable for measurement is detected, in this flow is a temporary error and not applicable to a continuous error.

In Step S304, the re-photographing determination unit 110 acquires, from the scanning controller 109, the size of the photoacoustic acquisition region designated by a user using the photographed-region designation unit 111, and compares the acquired size with a predetermined value. Then, in a case where the size of the photoacoustic acquisition region is smaller than the predetermined value, it is determined that the receiver 104 moves to the position 401 of the receiver 104 at a photographing start point. In such a case, a total photographing time is short, and the number of times of main scanning and sub-scanning by the receiver 104 are small, and therefore even though the receiver 104 moves to the position 401 to re-photograph, the total photographing time is not greatly increased.

When the receiver 104 moves to the position 403 just before an error occurs, or the start point 402 of a stripe for which photographing is currently being performed, to re-photograph, there is a possibility that a photograph condition slightly changes between before and after the error occurs, by an influence of body motion of the biological body 101. However, the receiver 104 thus moves to the photographing start point to re-photograph, so that the photograph conditions before and after the error occurs are the same, and continuity of data is maintained.

The predetermined value serving as the standard for determination as to whether the size of the photoacoustic acquisition region, which is designated by the user with the photographed-region designation unit 111, is small may be the number or times of main scanning or the number or times of sub-scanning, or may be the length of a total photographing time. That is, since the number of times of movement of the receiver in the main scanning direction and the sub-scanning direction is small, time loss is small even when photographing is performed again. Similarly, in a case where time required for acquiring acoustic waves until an error occurs is short, time loss is small. Alternatively, a configuration where a user sets the standard may be employed.

Since the scanning controller 109 holds the position of the receiver 104 at the photographing start point, information that scanning restarts from this position is transmitted to the scanning controller 109. In this flow, it is assumed that the size of the photoacoustic acquisition region designated by the user is smaller than the predetermined value.

In Step S305, the re-photographing determination unit 110 decides a position where the receiver 104 moves, on the basis of the results of determination in Step S303 and Step S304. In this flow, in Step S303, it is determined that the error is not such an error that continuously influences acquisition of a photoacoustic signal. In Step S304, it is determined that the size of the photoacoustic acquisition region designated by the user is smaller than the predetermined value. On the basis of these determination results, the re-photographing determination unit 110 decides that the receiver 104 returns to the position 401 at the photographing start point.

In a case where the determination result in Step S305 does not satisfy both the condition that the receiver 104 moves to the start point 402 of the stripe, and the condition that the receiver 104 moves to the photographing start position 401, it is decided that the receiver 104 moves to the position 403 just before an error occurs. When the error occurs, the receiver 104 stops scanning. Therefore, information that irradiation starts again from the current position of the receiver 104 held by the scanning controller 109 is transmitted. However, in a case where the scanning speed of the receiver 104 is considered, it is necessary to consider an acceleration distance until the receiver 104 performs scanning at an equal speed. At this time, the scanning controller 109 calculates a position displaced by the movement amount of the acceleration distance until the receiver 104 scans at an equal speed, from the position of the receiver 104, and scanning restarts from the position.

In any case, a position where irradiation can start again for re-photographing from a place where an error occurs and a photoacoustic signal cannot be acquired is transmitted to the scanning controller 109, and re-photographing can be performed from the position.

In Step S306, the re-photographing determination unit 110 transmits information calculated by the scanning controller 109 in Step S305. The scanning controller 109 receives the information to calculate a position where the receiver 104 moves, from information regarding the position of the receiver 104 held by the scanning controller 109, and re-photographing restarts from the position. The positional information held by the scanning controller 109 includes the current scanning position of the receiver 104, the position of the receiver 104 at the photographing start point, the position where the receiver 104 starts scanning in each stripe, and a scanning range of the receiver 104 during photographing.

As described above, according to the present invention, even in a case where an error occurs when characteristic information of the inside of an object is acquired by scanning with the receiver, it is determined whether or not re-photographing is possible in accordance with a content of the error. Then, in a case where re-photographing is possible, re-photographing is performed on the basis of a position of the receiver at the time of error occurrence, the content of the error, or the photographed size, thereby enabling suppression of increase in a photographing time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A photoacoustic apparatus comprising:
   a receiver that receives an acoustic wave from an object and converts the acoustic wave into an electric signal;
   a controller that controls an acoustic wave reception operation using the receiver; and
   a detector that detects an error,
   wherein the controller determines whether or not to change the acoustic wave reception operation on the basis of detection of the error by the detector.

2. The photoacoustic apparatus according to claim 1, wherein, in a case in which the error detected by the detector is an error that influences the acoustic wave reception operation, the controller determines whether or not to continue the acoustic wave reception operation depending on a content of the error.

3. The photoacoustic apparatus according to claim 2, further comprising:
a scanner that moves the receiver relative to the object,
wherein, in a case in which the controller determines to continue the acoustic wave reception operation, the controller determines a position to which the receiver is moved from a position where the acoustic wave is received when the error occurred.

4. The photoacoustic apparatus according to claim 3, wherein the controller resumes the acoustic wave reception operation from the position where the receiver is moved after an occurrence of the error.

5. The photoacoustic apparatus according to claim 3, wherein, in a case in which the error is not a continuous error, the controller causes the scanner to move the receiver to a position just before the error occurs.

6. The photoacoustic apparatus according to claim 3, wherein the scanner causes the receiver to perform scanning in a main scanning direction, and a sub-scanning direction intersecting with the main scanning direction,
the object is sectioned into a plurality of stripes corresponding to the main scanning direction, and
the controller causes the scanner to move the receiver to a start point of a stripe where the acoustic wave is received in the occurrence of the error, in a case where the error is a continuous error.

7. The photoacoustic apparatus according to claim 6, further comprising a designator that receives a designation from a user, the designation being relevant to an acoustic wave acquisition region where the acoustic wave from the object is acquired,
wherein, in a case in which the acoustic wave acquisition region is smaller in size than a predetermined value, the controller causes the scanner to move the receiver to move to a position where the reception of the acoustic wave has started.

8. The photoacoustic apparatus according to claim 7, wherein the predetermined value is decided on the basis of a number of times of movement of the receiver in the main scanning direction and the sub-scanning direction.

9. The photoacoustic apparatus according to claim 7, wherein the predetermined value is decided on the basis of time required for acquiring the acoustic wave until the occurrence of the error.

10. The photoacoustic apparatus according to claim 1, wherein the detector detects, as the error, an abnormality of communication.

11. The photoacoustic apparatus according to claim 1, further comprising an irradiator that radiates onto the object light that induces a photoacoustic wave in the object.

12. The photoacoustic apparatus according to claim 11, wherein the detector detects, as the error, that a quantity of light applied from the irradiator does not satisfy a predetermined reference criterion.

13. The photoacoustic apparatus according to claim 11, wherein the irradiator radiates the light to the object from the same side as the receiver with respect to the object.

14. The photoacoustic apparatus according to claim 7, further comprising an input unit that allows an input of the designation by the user.

15. A control method for a photoacoustic apparatus, the method comprising:
operating a receiver to receive an acoustic wave propagating inside an object and convert the acoustic wave into an electric signal using the receiver;
operating a controller to control an acoustic wave reception using the receiver; and
operating a detector to detect an error,
wherein, in the operating, the controller is controlled to determine whether or not to change the acoustic wave reception, on the basis of detection of the error by the detector.

16. The control method according to claim 15, further comprising:
operating the controller, in a case in which the detector detects an error that influences the acoustic wave reception, to determine whether or not to continue the acoustic wave reception operation depending on a content of the error.

17. The control method according to claim 16, further comprising:
operating the controller, in a case in which the controller determines to continue the acoustic wave reception operation, to determine a position to which the receiver is moved from a position where the acoustic wave is received when the error occurred.

18. The control method according to claim 17, further comprising:
operating the controller to resume the acoustic wave reception operation from the position where receiver is caused to move after an occurrence of the error.

19. The control method according to claim 17, further comprising:
operating the controller, in a case in which the error is not a continuous error, to cause a scanner to move the receiver to a position just before the error occurs.

20. The control method according to claim 17, wherein the receiver is moved in a main scanning direction and a sub-scanning direction intersecting with the main scanning direction, and the object is sectioned into a plurality of stripes corresponding to the main scanning direction, and
the method further comprising:
operating the controller to move the receiver to a start point of a stripe where the acoustic wave is received in the occurrence of the error, in a case where the error is a continuous error.

21. The control method according to claim 20, further comprising:
operating the controller, in a case in which an acoustic wave acquisition region designated by a user is smaller in size than a predetermined value, to move the receiver to a position where the reception of the acoustic wave has started.

22. The control method according to claim 21, wherein the predetermined value is decided on the basis of a number of times of movement of the receiver in the main scanning direction and the sub-scanning direction.

23. The control method according to claim 21, wherein the predetermined value is decided on the basis of time required for acquiring the acoustic wave until the occurrence of the error.

24. The control method according to claim 15, wherein the detector detects, as the error, an abnormality of communication.

25. The control method according to claim 15, wherein the detector detects, as the error, that a quantity of light applied from the irradiator does not satisfy a predetermined reference criterion.

26. The control method according to claim 15, further comprising:
   operating a processor to acquire characteristic information on an inside of the object on the basis of the electric signal.

27. The photoacoustic apparatus according to claim 1, further comprising:
   a processor that acquires characteristic information on an inside of the object on the basis of the electric signal.

\* \* \* \* \*